(12) United States Patent
Piazza et al.

(10) Patent No.: US 9,468,646 B2
(45) Date of Patent: Oct. 18, 2016

(54) INCREASED DOSAGE OF EFAVIRENZ FOR THE TREATMENT OF CANCER

(71) Applicant: Alienor Farma, Pessac (FR)

(72) Inventors: Pier Vincenzo Piazza, Bordeaux (FR); Nadine Houede, Beychac et Cailleau (FR); Audrey Laroche-Clary, Bordeaux (FR)

(73) Assignee: ALIENOR FARMA, Pessac (FR)

( * ) Notice: Subject to any disclaimer, the term of this patent is extended or adjusted under 35 U.S.C. 154(b) by 0 days.

(21) Appl. No.: 14/761,481

(22) PCT Filed: Jan. 23, 2013

(86) PCT No.: PCT/IB2013/000227
§ 371 (c)(1),
(2) Date: Jul. 16, 2015

(87) PCT Pub. No.: WO2014/114971
PCT Pub. Date: Jul. 31, 2014

(65) Prior Publication Data
US 2015/0366871 A1    Dec. 24, 2015

(51) Int. Cl.
*A61K 31/536* (2006.01)
*C07D 265/18* (2006.01)
*C12Q 1/68* (2006.01)

(52) U.S. Cl.
CPC .......... *A61K 31/536* (2013.01); *C12Q 1/6886* (2013.01); *C07D 265/18* (2013.01); *C12Q 2600/106* (2013.01); *C12Q 2600/156* (2013.01)

(58) Field of Classification Search
CPC . C07D 265/18; A61K 31/535; A61K 31/536
USPC ....................................... 514/230.5
See application file for complete search history.

(56) References Cited

U.S. PATENT DOCUMENTS

2006/0166970 A1* 7/2006 Spadafora ............ A61K 31/536
514/220

FOREIGN PATENT DOCUMENTS

WO    9964405 A1    12/1999
WO    03055493 A1    7/2003
(Continued)

OTHER PUBLICATIONS

Houede, Nadine et al, J. Clin. Oncology, 2012, vol. 30, supplement, abstract 251.*

(Continued)

*Primary Examiner* — Kamal Saeed
*Assistant Examiner* — Janet L Coppins
(74) *Attorney, Agent, or Firm* — Banner & Witcoff, Ltd.

(57) ABSTRACT

The invention is based on the finding that an increased daily dose of Efavirenz should be used for the treatment of cancer compared to the daily dose used in the treatment of AIDS. The invention thus relates to the use of Efavirenz for preparing a medicament intended for the treatment of cancer, wherein Efavirenz is administered at a dose generating an Efavirenz plasma concentration in said patient superior to 3000 ng/ml. It further relates to the use of Efavirenz for preparing a medicament intended for the treatment of cancer, wherein Efavirenz is administered at a daily dose of at least 1800 mg, in particular between 1800 and 2200 mg. It also relates to the use of Efavirenz for preparing a medicament intended for the treatment of cancer, in which the daily dose of Efavirenz is optimized after administration of a preliminary daily dose and measure or Efavirenz plasma concentration. It also relates to a unique dosage form of Efavirenz, comprising Efavirenz in an amount generating an Efavirenz plasma concentration in said patient superior to 3000 ng/ml, and a pharmaceutically acceptable carrier.

11 Claims, 5 Drawing Sheets

(56) References Cited

FOREIGN PATENT DOCUMENTS

| WO | 2006069812 A2 | 7/2006 |
| WO | 2008144458 A1 | 11/2008 |
| WO | 2011151786 A2 | 12/2011 |

OTHER PUBLICATIONS

International Search Report issued in corresponding International Application No. PCT/IB2013/000227, dated Sep. 12, 2013.
Houede et al., First Results of a Phase II Trial to Assess the Efficacy of Efavirenz in Patients with Metastatic Androgen-Independent Prostate Cancer, J Clin Oncol, 30, 2012.
Institut Bergonié, Phase I Dose Escalation Trial of Efavirenz for Patients with Solid Tumours or Non-Hodgkin Lymphoma in Therapeutic Failure, Clinical Trials.gov, Jun. 14, 2013, pp. 1-2.
Institut National Du Cancer, Essai de Phase 1 Monocentrique Évaluant la Tolérance de l'Éfavirenz, Chez des Patients Ayant Une Tumeur Solide Ou Un Lymphome Non Hodgkinien Réfractaire, les Essais Cliniques—Registre des Essais Cliniques Français en Cancérologie, Dec. 5, 2012, pp. 1-3.
Ashworth et al., Zfa is an Expressed Retroposon Derived From an Alternative Transcript of the Zfx Gene, The Embo Journal, vol. 9, No. 5, 1990, pp. 1529-1534.
Babich et al., Association of Some Potential Hormone Response Elements in Human Genes With the Alu Family Repeats, Gene, vol. 239, pp. 341-349, 1999.
Balani et al., Nonlinear Pharmacokinetics of Efavirenz (dmp-266), a Potent HIV-1 Reverse Transcriptase Inhibitor, in Rats and Monkeys, Drug Metabolism and Disposition, vol. 27 No. 1, pp. 41-45, Jan. 1999.
Cheson et al., Revised Response Criteria for Malignant Lymphoma, Journal of Clinical Oncology, vol. 25, No. 5, Feb. 2007, pp. 579-586.
Cho et al., Hypermethylation of CpG Island Loci and Hypomethylation of Line-1 and Alu Repeats in Prostate Adenocarcinoma and Their Relationship to Clinicopathological Features, Journal of Pathology, vol. 211, Nov. 2006, pp. 269-277.
Cordaux et al., The Impact of Retrotansposons on Human Genome Evolution, Nature Reviews Genetics, October, vol. 10, 2009, pp. 691-703.
Doucet et al., Characterization of Line-1 Ribonucleoprotein Particles, PLOS Genetics, vol. 6, Oct. 2010, pp. 1-19.
Egge-Jacobsen et al., Automated, Fast, and Sensitive Quantification of Drugs in Human Plasma by LC/LC-MS, Ther Drug Monit, vol. 26, No. 5, Oct. 2004, pp. 546-562.
Eisenhauer et al., New Response Evalutation Criteria in Solid Tumours: Revised Recist Guideline (version 1.1), EJC 45, 2009: 228-245.
Estecio et al., Line-1 Hypomethylation in Cancer is Highly Variable and Inversely Correlated With Microsatellite Instability, PLOS One, Issue 5, May 2007, pp. 1-7.
Mello et al., Successful Efavirenz Dose Reduction Guided by Therapeutic Drug Monitoring, Antiviral Therapy, vol. 16, 2011, pp. 189-197.
Feuchter-Murthy et al., Splicing of a Human Endogenous Retrovirus to a Novel Phospholipase A2 Related Gene, Nucleic Acids Research, vol. 21, No. 1, 1993, 135-143.
Ferrigno et al., Transposable B2 Sine Elements Can Provide Mobile RNA Polymerase II Promoters, Nature Genetics, vol. 28, 2001, pp. 77-81.
Gasior et al., Characterization of Pre-Insertion Loci of de Novo L1 Insertions, Gene, 2007, Apr. 1; 390(1-2): pp. 190-198. Epub 2006, Sep. 12.
Gilbert et al., Multiple Fates of L1 Retrotransposition Intermediates in Cultured Human Cells, Molecular and Cellular Biology, vol. 25, No. 17, Sep. 2005, pp. 7780-7795.
Goodier et al., Retrotransposons Revisited: The Restraint and Rehabilitation of Parasites, Cell, 135, Oct. 3, 2008, pp. 23-35.
Han et al., Transcriptional Disruption by the L1 Retrotransposon and Implications for Mammalian Transcriptomes, Nature, vol. 429, May 2004, pp. 268-274.
Islam et al., The Long Terminal Repeat of VL30 Retrotransposons Contains Sequences That Determine Retinoic Acid-Induced Transcription in Cultured Keratinocytes, Journal of Biological Chemistry, vol. 268, No. 5, Feb. 15, 1993, pp. 3251-3259.
Kappelhoff et al., Are Adverse Events of Nevirapine and Efavirenz Related to Plasma Concentration?Antiviral Therapy, vol. 10, 2005, pp. 489-498.
Kazazian et al., Mobile Elements and Disease, Current Opinion in Genetics & Development, vol. 8, 1998, pp. 343-350.
Kwara et al., Genetic Polymorphisms Are Predictors of Efavirenz Mid-Dose Concentration in HIV-Infected Patients, Aids, Oct. 23, 2009, pp. 2101-2106.
Kwara et al., CYP2B6 (c.516G® T) and CYP2A6 (*9B and/or *17) Polymorphisms Are Independent Predictors of Efavirenz Plasma Concentrations in HIV-Infected Patients, British Journal of Clinical Pharmacology vol. 67, Issue 4, 2009, pp. 427-436.
Lee et al., Landscape of Somatic Retrotransposition in Human Cancers, Science, vol. 337, Aug. 24, 2012 pp. 967-971.
Lin et al., Nuclear Receptor-Induced Chromosomal Proximity and DNA Breaks Underlie Specific Translocations in Cancer, Cell, 139, Dec. 11, 2009, pp. 1069-1083.
Mangiacasale et al., Exposure of Normal and Transformed Cells to Nevirapine, a Reverse Transcriptase Inhibitor, Reduces Cell Growth and Promotes Differentiation, Oncogene, 22, May 2003, pp. 2750-2761.
Marzolini et al., Simultaneous Determination of the HIV Protease Inhibitors Indinavir, Amprenavir, Saquinavir, Ritonavir, Nelfinavir and the Non-Nucleoside Reverse Transcriptase Inhibitor Efavirenz by High-Performance Liquid Chromatography After Solid-Phase Extraction, Journal of Chromatography b, 740, 2000, 43-58.
Marzolini et al., Efavirenz Plasma Levels Can Predict Treatment Failure and Central Nervous System Side Effects in HIV-1-Infected Patients, Aids, 15, Jan. 5, 2001, pp. 71-75.
Nekrutenko et al., Transposable Elements are Found in a Large Number Of Human Protein-Coding Genes, Trends in Genetics, vol. 17, No. 11, Nov. 2001, pp. 619-621.
Neuhausen et al., DNA Methylation Alterations in Urothelial Carcinoma, Cancer Biology & Therapy, vol. 5, Issue 8, Aug. 2006, pp. 993-1001.
Norris et al., Identification of a New Subclass of Alu DNA Repeats Which Can Funcation As Estrogen Receptor-Dependent Transcriptional Enhancers, Journal of Biological Chemistry,vol. 270, No. 39, Sep. 29, 1995, pp. 22777-22782.
O'Quigley et al., Consistency of Continual Reassessment Method Under Model Misspecification, Biometrics, 83, 2, 1996, pp. 395-405.
Pattamadilok et al., Line-1 Hypomethylation Level as a Potential Prognostic Factor for Epithelial Ovarian Cancer, Int J Gynecol Cancer, 18, 2008, pp. 711-717.
Rezk et al., Full Validation of An Analytical Method for the HIV-Protease Inhibitor Atazanavir in Combination With 8 Other Antiretroviral Agents and its Applicability to Therapeutic Drug Monitoring, Ther Drug Monit, vol. 28, No. 4, Aug. 2006, pp. 517-525.
Roman-Gonzalez, Promoter Hypothylation of the Line-1 Retrotransposable Elements Activates Sense/Antisense Transcription and Marks the Progression of Chronic Myeloid Leukemia, Oncogene, 24, 2005, pp. 7213-7223.
Rotger et al., Predictive Value of Known and Novel Alleles of CYP2B6 for Efavirenz Plasma Concentrations in HIV-Infected Individuals, Clin Pharmacol Ther., vol. 81, No. 4, Apr. 2007, pp. 557-566.
Scher et al., Design and End Points of Clinical Trials for Patients With Progressive Postate Cancer and Castrate Levels of Testosterone: Reccomendations of the Prostate Cancer Clinical Trials Working Group, vol. 26, No. 7, Mar. 1, 2008, pp. 1148-1159.
Schulz et al., Methylation of Endogenous Human Retroelements in Health and Disease, Curr Top Microbiol Immunol, 310, 2006, pp. 211-250.

(56) References Cited

OTHER PUBLICATIONS

Shaffer et al., Breaking the Rules of Cancer, Nat Med, vol. 12, No. 1, Jan. 2006, pp. 14-15.
Sinibaldi-Vallebona et al., A Role for Endogenous Reverse Transcriptase in Tumorigenesis and As a Target in Differentiating Cancer Therapy, Genes Chromosomes Cancer, vol. 45, Jan. 2006, pp. 1-10.
Speek, Antisense Promoter of Human L1 Retrotransposon Drives Transcription of Adjacent Cellular Genes, Molecular and Cellular Biology, vol. 21, No. 6, Mar. 2001, pp. 1973-1985.
Takahashi et al., Conventional HPLC Method Used for Simultaneous Determination of the Seven HIV Protease Inhibitors and Nonnucleoside Reverse Transcription Inhibitor Efavirenz in Human Plasma, Biol Pharm Bull, vol. 28, No. 7, 2005, 1286-1290.
Tangkijvanich et al., Serum LINE-1 Hypomethylation as a Potential Prognostic Marker for Hepatocellular Carcinoma, Clin Chim Acta,379, Apr. 2007, 127-133.
Heine et al., Fast and Simultaneous Determination of Darunavir and Eleven Other Antiretroviral Drugs for Therapeutic Drug Monitoring: Method Development and Validation for the Determination of All Currently Approved HIV Protease Inhibitors and Non-Nucleoside Reverse Transcriptase Inhibitors in Human Plasma by Liquid Chromatography Coupled With Electrospray Ionization Tandem Mass Spectrometry, Rapid Communications in Mass Spectrometry, 21, 2007, pp. 2505-2514.
Tomilin, Control of Genes by Mammalian Retroposons, International Review of Cytology, vol. 186, 1999, pp. 1-48.
Tomlins et al., Recurrent Fusion of TMPRSS2 and ETS Transcription Factor Genes in Prostate Cancer, Science, vol. 310, Oct. 28, 2005, pp. 644-648.
Luin et al., Absence of a Relation Between Efavirenz Plasma Concentrations and Toxicity-Driven Efavirenz Discontinuations in the EuroSida Study, Antiviral Therapy, 14, 2009, 75-83.
Veldkamp et al., The Steady-State Pharmacokinetics of Efavirenz and Nevirapine When Used in Combination in Human Immunodeficiency Virus Type 1-Infected Persons, Journal of Infectious Diseases, 184, Jul. 1, 2001, 37-42.
Vilani et al., Antiretrovirals: Simultaneous Determination of Five Protease Inhibitors and Three Nonnucleoside Transcriptase Inhibitors in Human Plasma by a Rapid High-Performance Liquid Chromatography-Mass Spectrometry Assay, Therapeutic Drug Monitoring, vol. 23, Aug. 2001, pp. 380-388.
Whitelaw et al., Retrotransposons as Epigenetic Mediators of Phenotypic Variation in Mammals, Nature Genetics, vol. 27, Apr. 2001, pp. 361-365.
Wyen et al., Impact of CYP2B6 983T>C Polymorphism on Non-Nucleoside Reverse Transcriptase Inhibitor Plasma Concentrations in HIV-Infected Patients, Journal of Antimicrobial Chemotherapy, vol. 61, 2008, pp. 914-918.

* cited by examiner

INCREASED DOSAGE OF EFAVIRENZ FOR THE TREATMENT OF CANCER

RELATED APPLICATION DATA

This application is a National Stage Application under 35 U.S.C. 371 of co-pending PCT application number PCT/IB2013/000227 designating the United States and filed Jan. 23, 2013 which is hereby incorporated by reference in its entirety.

FIELD OF THE INVENTION

The invention is in the field of cancer treatment, and provides a method for treating cancer with Efavirenz, with a daily dose of Efavirenz sufficient to achieve an Efavirenz plasma concentration of at least 3000 ng/ml. In many patients, such an Efavirenz plasma concentration will be obtained with a daily dose of Efavirenz of 1800 mg. The invention thus also relates to a unique dosage form of Efavirenz, comprising at least 1800 mg of Efavirenz and a pharmaceutically acceptable carrier. The invention also provides a method for optimizing Efavirenz daily dose in cancer patients based on the monitoring of Efavirenz plasma concentration.

BACKGROUND ART

Cancer progression has been more and more associated to new genetic alterations or dedifferentiation processes.

More specifically, in prostate cancer, prostate cancer cells initially require androgens to proliferate and the progression of the disease is stopped by hormone therapies that decrease androgen signaling. Unfortunately, in many cases, after variable periods of time, prostate cancer becomes resistant to hormone therapies, entering the stage of "castration-resistant prostate cancer" or "hormone-refractory prostate cancer" and starts progressing again.

This renewed progression of prostate cancer is due to the selection over time of a population of cancer cells that can proliferate with low concentrations of androgens or in the total absence of them. This hormone resistance is mediated by two types of mechanisms:

(1) Androgen-dependent resistance, in which cancer cells are still dependent from androgen signaling but develop: (a) a hyperactivity of the androgen receptors (AR) that now need little or no androgens to be activated and/or (b) an ectopic production of androgens that are now synthesized autonomously by cancer cells which are insensitive to hormone suppressive therapies.

(2) Androgen-independent resistance, in which cancer cells become completely independent from androgen signaling because of (a) a profound de-differentiation of the cell, often accompanied by epithelial-mesenchymal transition (EMT), which increases malignancy and confer the ability to proliferate without androgens; and/or (b) the acquisition of an intrinsic resistance to apoptosis mediated by the over-expression of anti-apoptotic proteins, which counteract the cell death normally induced by the absence of androgens.

Clearly, efficient treatments of hormone-refractory prostate cancer need to target both androgen-dependent and androgen-independent mechanisms of resistance.

Several pharmaceutical companies are developing a second generation of hormone therapies that try to overcome androgen-dependent mechanisms of resistance either using better antagonists of the androgen receptors (MDV3100, Medivation) or by blocking the ectopic production of androgens by cancer cells (abiraterone acetate, J&J; and TAK 700, Takeda) and also by targeting both mechanisms (TOK-001, Tokai Pharmaceuticals).

However, there is currently no efficient treatment of androgen-independent hormone-refractory prostate cancer. In addition, it may be difficult or costly to determine if a hormone-refractory prostate cancer is based on an androgen-dependent or an androgen-independent mechanism of resistance. There is thus a need for new treatments able to target both androgen-dependent and androgen-independent hormone-refractory prostate cancer. Similarly, there is also a need for treatments able to target other progressing cancers characterized by cell de-differentiation.

LINE-1 (L1) is a mammalian family of retrotransposable elements, i.e. mobile DNA sequences able to relocalize throughout the genome via RNA intermediates that are reverse-transcribed and inserted at new genomic locations. The canonical, full-length L1 element is ~6 kilobases (kb) in length and has two open reading frames, ORF1 and ORF2 coding for two proteins. ORF1 codes for 40 kDa RNA binding protein. ORF2 codes for a 149 kDa protein which is a reverse transcriptase (RT) that also has an endonuclease domain. This molecular machinery makes L1 elements among the few autonomous transposable elements in the human genome and the more abundant by mass. Each cell contains approximatively 500,000 copies of L1 accounting for 17% of the human genome. Most of L1 copies are truncated but it is calculated that there are approximatively 100 copies of full length L1 elements that encode for functional proteins.

The ORF2-produced L1-reverse transcriptase protein (L1-RT) has been increasingly involved in the pathophysiology of cancer. In normal adult tissues, L1-RT activity is strongly repressed by methylation of its promoter (Schulz, 2006). In contrast, L1-RT activity is strongly activated in several types of cancer.

Hypomethylation of LINE-1 is the main candidate mechanism for the pathological reactivation of this retrotransposon during cancer progression, and has been reported in several human malignant neoplasiae, such as colon (Estecio, 2007), liver (Tangkijvanich, 2007), prostate (Cho, 2007), bladder (Neuhausen, 2006), ovary (Pattamadilok, 2008), leukemia (Roman-Gomez, 2005). In addition, the degree of LINE-1 hypomethylation has been reported to be correlated with tumor progression and prognosis in several types of cancer; ovary (Pattamadilok, 2008), prostate (Cho, 2007), liver (Tangkijvanich, 2007). The potential influence of LINE-1 on cancer is strengthened by direct functional tests that have evidenced a strong correlation between L1-RT activity and the proliferation-transformation status of various cancer cell lines in culture (Mangiacasale 2003). Finally, an increase in the activity of L1-RT in human epithelial cancers has been recently demonstrated measuring L1-RT dependent somatic retrotransposition (Lee, 2012).

In addition to hypomethylation, a supplementary more specific mechanism seems to mediate the overexpression of L1-RT in hormone-refractory prostate cancer cells. Thus, in poorly differentiated hormone-refractory prostate cancer cells, it has been shown that the over expression of L1-RT is due to the low expression of the proteins PIWIs. PIWIs proteins are highly expressed in differentiated prostate cells and inhibit the transcription of LINE-1 (Lin, 2009).

The reactivation of LINE-1 in cancer cells is known to cause retrotransposition events which, in turn, produce dramatic consequences like mutations and DNA double strand breaks, a series of events that rapidly leads to global genetic instability (Gilbert, 2005; Gasior, 2007). In addition to genetic instability, L1-proteins seem also able to control gene expression epigenetically (for review see Sinibaldi-Vallebona, 2006).

L1-proteins can induce genetic instability by several mechanisms. The most evident is insertional mutagenesis, a process through which the insertion of a retroelement within a protein-coding gene can be equivalent to a functional gene "knock-out" (reviewed by Kazazian, 1998), or, on the contrary, give rise to a new coding unit (Nekrutenko, 2001). Retrotransposons can also act as cis-acting transcriptional regulatory sequences, providing DNA binding sites for a variety of Pol III- and Pol II-associated transcription factors (reviewed by Tomilin, 1999), and hormone—(Norris, 1995; Babich, 1999) and retinoic acid—(Islam, 1993) receptor-dependent transcriptional enhancers. Retrotransposition can also influence posttranscriptional regulation by providing novel splicing sites in coding genes (Ashworth, 1990; Feuchter-Murthy, 1993) or by insertion into specific introns it can considerably reduce the transcriptional elongation of the targeted gene (Han, 2004). Furthermore, LINE-1 sequences can provide new promoters in the sense (Ferrigno, 2001) or antisense (Speek, 2001) orientation, thus triggering the activation of existing genes and modulating tissue-specific expression. Finally, L1-RT mediated somatic retrotransposition has been recently proposed as a selection mechanism increasing the presence of the most aggressive cancer clones in epithelial cancers (Lee, 2012).

In addition to genetic instability, the activity of L1-RT seems also able to influence epigenetically the cell fate providing phenotypic variations in mammals (for a review, see Whitelaw, 2001). Although not all molecular steps are fully understood, the epigenetic control exerted by L1-RT has been recently shown by the profound reprogramming of the transcriptome, induced in tumor cell by the treatment with pharmacological inhibitors of L1-RT. This reprogramming involves both protein-coding and non-coding sequences associated with a global reorganization of the nuclear chromatin conformation, Further studies now suggest that L1-RT participates to a tumor-protecting mechanism by profoundly altering the miRNA-mediated regulation of transcription. L1-RT seems able to inactivate double stranded miRNA primary transcripts by shifting the equilibrium towards RNA/DNA hybrid structures via reverse transcription.

Recently the over-expression of L1-ORF2 protein, which contains the RT domain, has been linked to specific pathophysiological processes involved in prostate cancer progression and malignancy. In prostate cancer, the activation of the AR (Androgen Receptor) induces DNA recombination at specific site in the genome (Lin, 2009). These events involve translocation of the 5' untranslated region of the AR target gene TMPRSS2 to two members of the ETS family of genes, ERG and ETV1 (Tomlins, 2005). These rearrangements lead to androgen dependent over-expression of ETS transcription factors, most frequently the proto-oncogenes ETV1 or ERG, which have been proposed as key factors in stimulating the development and aggressiveness of prostate cancers (Shaffer, 2006). This site specific AR-induced translocation event needs the recruitment of L1-ORF2 protein. Thus, over expression of L1-RT proteins greatly enhances AR-induced site specific translocation of TMPRSS2, while competition of the active proteins with an inactive mutant greatly reduces it.

Supporting a causal relationship between LINE-1 activity and tumor progression, suppression by RNA interference of L1-RT in a human melanoma cell line (A375) results in a strong inhibition of cell proliferation in vitro (pure cytostatic effect) and tumor growth in vivo in xenografted mice (Sciamanna, 2005; WO2006069812A2).

An increasing body of compelling evidences thus suggests that the transcriptional reactivation of LINE-1 expression—notably suppressed or down regulated in normal cells—plays a major causative role in the onset and progression of human cancer malignancy. For these reasons, the pharmacological antagonism of these cancer specific proteins appears as a very promising target for developing new therapies in oncology.

Pharmacological inhibitors of L1-RT have several effects that indicate that these compounds are capable to counteract androgen-independent mechanism of resistance. Two L1-RT inhibitors, Efavirenz and Nevirapine, have been studied in vitro and in vivo. These molecules are non-nucleoside reverse transcriptase inhibitors (NNRTIs) and have been initially developed for the treatment of HIV infection since they block the reverse transcriptase of the HIV virus and antagonize its replication. Both Nevirapine and Efavirenz are able to inhibit the reverse transcriptase activity of L1-RT in human tumor cell lines (see WO03055493A1).

L1-RT inhibitors can counteract cancer development by three complementary mechanisms: inhibition of proliferation of cancer cell lines (see Sciamanna, 2005; WO03055493A1; WO2006069812A2), induction of cell differentiation and antagonism of epithelial-mesenchymal transition (EMT) (see Sciamanna, 2005; WO03055493A1; WO2006069812A2), and inhibition of intrinsic resistance to apoptosis. Concerning inhibition of intrinsic resistance to apoptosis, L1-RT inhibitors decrease the expression of anti-apoptotic proteins such as Bcl2 and are also very effective in inducing cell death in prostate cancer cell lines that over express proteins of the Bcl2 family such as Bcl-xL that protects them from apoptosis and makes them resistant to treatment.

L1-RT inhibitors thus antagonize tumor progression by acting on multiple cellular mechanisms. These cellular mechanisms play an important role in the pathophysiology of hormone-refractory prostate cancer, and this disease is therefore a natural target for testing the therapeutic effects of L1-RT inhibitors in humans. However, dedifferentiation, epithelial-mesenchymal transition (EMT) and resistance to apoptosis play an important role in pathophysiology of several types of cancers. As a consequence, L1-RT inhibitors can reasonably be expected to be a useful treatment for other cancer pathologies still awaiting treatment and in particular for epithelial cancers (Lee, 2012).

Non-nucleoside RT inhibitors (NNRTIs), such as Efavirenz and nevirapine, have initially been developed as inhibitors of the HIV reverse transcriptase.

Figure 1:
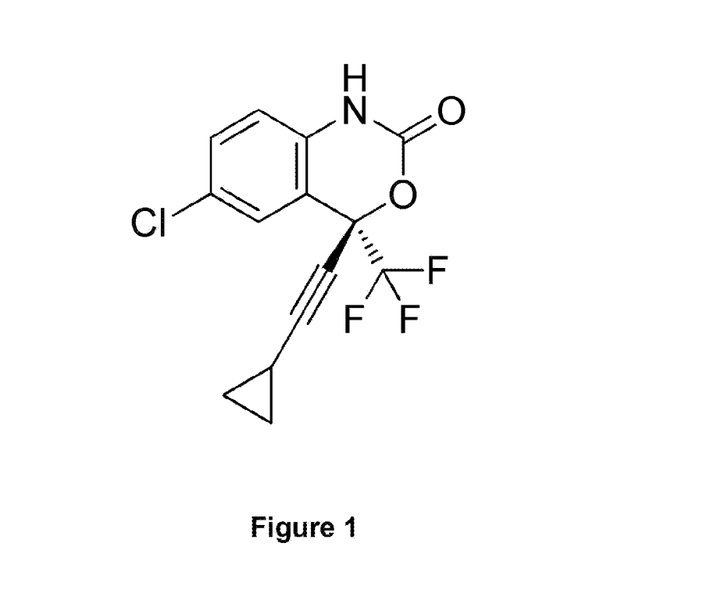
FIG. 1: Molecular structure of Efavirenz. (S)-6-chloro-(cyclopropylethynyl)-1,4-dihydro-4-(trifluoromethyl)-2H-3,1-benzoxazin-2-one.

Efavirenz (see formula in FIG. 1) is a benzoxazinone and is a particularly well tolerated molecule and used for the treatment of AIDS at the daily dosage of 600 mg/day. Data obtained in humans treated with 600 mg/day of Efavirenz show that plasma concentrations above 1500 ng/ml are observed in approximately 70-80% (Marzolini, 2001) of the subjects.

It has been shown in rats treated with Efavirenz (WO03555493) that tumor progression is inhibited for a dose of approximately 5 mg/kg/day (1 mg/rat/day intraperitoneally, weight of one rat approximately 200 g). In parallel, a pharmacokinetic study in rats published by Balani et al (1999) has shown that an intravenous injection of 5 mg/kg of Efavirenz gives a maximal plasma concentration of the drug of 5 µM, corresponding to 1578 ng/ml.

The daily dosage of 600 mg/day of Efavirenz used for the treatment of AIDS could thus reasonably be expected to be also efficient for the treatment of cancer in humans.

A clinical trial of the use of Efavirenz in the treatment of hormone-refractory prostate cancer was thus launched based on a dose of Efavirenz of 600 mg/day, expecting a response in 70-80% of patients.

SUMMARY OF THE INVENTION

Surprisingly, while an Efavirenz plasma concentration of at least 1500 ng/ml was observed in 70% of the treated patients, only 28% of all treated patients showed non-progressions for PSA levels at 3 months, the disease continuing to progress in 72% of patients. In contrast, in patients with Efavirenz plasma concentrations above 3000 ng/ml, the proportions were inverted, PSA progression being observed in only about 29% of the subjects (about 71% of non-progressors). Therefore, the inventors unexpectedly found that in humans Efavirenz dose should be higher for the treatment of cancer than for the treatment of AIDS and should generate an Efavirenz plasma concentration of at least 3000 ng/ml. This can be obtained in most patients using a daily dose of Efavirenz of 1800 mg or 2200 mg, i.e. a much higher daily dose than that useful for treatment of HIV infection.

The present invention thus concerns a method for treating cancer in a patient in need thereof, comprising administering to said patient a therapeutically efficient amount of Efavirenz, wherein said therapeutically efficient amount of Efavirenz generates an Efavirenz plasma concentration in said patient superior to 3000 ng/ml. Similarly, the invention also concerns the use of Efavirenz, or a composition comprising Efavirenz and a pharmaceutically acceptable carrier, for treating cancer in a patient in need thereof, wherein Efavirenz is administered at a dose generating an Efavirenz plasma concentration in said patient superior to 3000 ng/ml. The invention further concerns Efavirenz, or a composition comprising Efavirenz and a pharmaceutically acceptable carrier, for use in the treatment of cancer in a patient, wherein Efavirenz is administered to the patient at a dose generating an Efavirenz plasma concentration in said patient superior to 3000 ng/ml. The invention also concerns the use of Efavirenz for preparing a medicament intended for the treatment of cancer in a patient, wherein Efavirenz is administered to the patient at a dose generating an Efavirenz plasma concentration in said patient superior to 3000 ng/ml. The dose is preferably administered on a daily basis (daily dose).

Preferably, a suitable or optimal Efavirenz daily dose for the patient is determined based on Efavirenz plasma concentration monitoring. Alternatively or in addition, a suitable or optimal Efavirenz daily dose for the patient may also be determined based on genotyping of the patient's CYP2B6 alleles.

In a preferred embodiment, the daily dose of Efavirenz administered to the patient is at least 1800 mg, in particular between 1800 and 2200 mg, such as 1800, 1900, 2000, 2100 or 2200 mg. Preferably, such a daily dose is administered to a patient who does not have two loss or decrease of function CYP2B6 alleles. For a patient who has two loss or decrease of function CYP2B6 alleles, the daily dose of Efavirenz may be lower, such as 600 mg.

The invention also relates to a method for treating cancer in a patient in need thereof, comprising administering to said patient a therapeutically efficient amount of Efavirenz, wherein the daily dose of Efavirenz administered to the patient is at least 1800 mg, in particular between 1800 and 2200 mg, such as 1800, 1900, 2000, 2100 or 2200 mg. Similarly, the invention also concerns the use of Efavirenz, or a composition comprising Efavirenz and a pharmaceutically acceptable carrier, for treating cancer in a patient in need thereof, wherein Efavirenz is administered at a daily dose of at least 1800 mg, in particular between 1800 and 2200 mg, such as 1800, 1900, 2000, 2100 or 2200 mg. The invention further concerns Efavirenz, or a composition comprising Efavirenz and a pharmaceutically acceptable carrier, for use in the treatment of cancer in a patient, wherein Efavirenz is administered to the patient at a daily dose of at least 1800 mg, in particular between 1800 and 2200 mg, such as 1800, 1900, 2000, 2100 or 2200 mg.

The invention also concerns the use of Efavirenz for preparing a medicament intended for the treatment of cancer in a patient, wherein Efavirenz is administered to the patient at a daily dose of at least 1800 mg, in particular between 1800 and 2200 mg, such as 1800, 1900, 2000, 2100 or 2200 mg.

The present invention also relates to a method for treating cancer in a patient in need thereof, comprising:
  a) optionally, genotyping gene CYP2B6 of said patient,
  b) administering a preliminary daily dose $D_P$ of Efavirenz to the patient,
  c) monitoring Efavirenz plasma concentration in the patient,
  d) administering an optimized daily dose $D_O$ of Efavirenz to the patient, wherein:
    i) if the patient's Efavirenz plasma concentration is inferior to 3000 ng/ml, then the optimized daily dose $D_O$ of Efavirenz is increased compared to the preliminary daily dose $D_P$,
    ii) if the patient's Efavirenz plasma concentration is superior to 3000 ng/ml, then the optimized daily dose $D_O$ of Efavirenz is the same as or lower than the preliminary daily dose $D_P$.

In a preferred embodiment of the above method of treatment involving Efavirenz dose adaptation based on Efavirenz plasma concentration monitoring, the preliminary daily dose $D_P$ of Efavirenz administered to the patient is 1800 mg, although lower preliminary daily dose $D_P$ of Efavirenz may be used, such as 600 or 1200 mg for instance. Similarly, the invention also concerns the use of Efavirenz, or a composition comprising Efavirenz and a pharmaceutically acceptable carrier, for treating cancer in a patient in need thereof, wherein Efavirenz dose is optimized as indicated above. The invention further concerns Efavirenz, or a composition comprising Efavirenz and a pharmaceutically acceptable carrier, for use in the treatment of cancer in a patient, wherein Efavirenz dose is optimized as indicated above. The invention also concerns the use of Efavirenz for preparing a medicament intended for the treatment of cancer in a patient, wherein Efavirenz dose is optimized as indicated above.

The methods of treatment according to the invention are applicable to any type of cancer. In a preferred embodiment, the patient is suffering from an epithelial cancer, in particular from prostate cancer, lung cancer, ovarian cancer, colorectal cancer, or melanoma. In a particularly preferred embodiment, the patient is suffering from prostate cancer, in particular from hormone refractory prostate cancer, including androgen-independent hormone refractory prostate cancer.

While the method may be used in any (preferably human) patient suffering from any type of cancer, it is more particularly intended for patients who are not also infected by human immunodeficiency virus (HIV). However, it may also be used for HIV-infected individuals suffering at the same time of a cancer. The Efavirenz dose is then simply adapted in order to be efficient on cancer cells.

The present invention also relates to a unique dosage form of Efavirenz, comprising Efavirenz in an amount generating an Efavirenz plasma concentration in said patient superior to 3000 ng/ml upon administration of at most two (i.e. one or two) units of said unique dosage form, and a pharmaceutically acceptable carrier. When only one unit of said unique dosage form of Efavirenz is able to generate upon administration to a patient an Efavirenz plasma concentration in said patient superior to 3000 ng/ml, the Efavirenz amount in said unique dosage form is preferably superior or equal to 1800 mg, and may preferably be between 1800 and 2200 mg, such as 1800, 1900, 2000, 2100 or 2200 mg. Alternatively, when the unique dosage form of Efavirenz is designed so that a plasma Efavirenz concentration of at least 3000 ng/ml is obtained in most patients by administration of two units of the unique dosage form, the Efavirenz amount in said unique dosage form is preferably superior or equal to 900 mg, in particular between 900 and 1100 mg, such as 900, 950, 1000, 1050 or 1100 mg. In any case, the unique dosage form of Efavirenz may be in any appropriate form, such as in the form of a tablet, a capsule, a powder, or granules.

BRIEF DESCRIPTION OF THE DRAWINGS

FIG. 4: Intention to treat (ITT) analysis of the progression free survival in hormone refractory prostate cancer patients as a function of Efavirenz plasma concentrations. (A) Progression free survival was significantly higher (Median survival=17 versus 3 months, P=0.0182; Log-rank Mantel-Cox's test) in patients with high plasma concentrations of Efavirenz (>3000 ng/ml group) compared to patients with low (<1500 ng/ml) or intermediate (1500-3000 ng/ml) plasma concentrations of Efavirenz. The latest two groups did not differ (P=0.8602, Log-rank Mantel-Cox's test) and were cumulated for statistical analysis. (B) The increase in the daily dose of Efavirenz up to 1200 mg/day in subjects with originally low (<3000 ng/ml) plasma Efavirenz concentrations (Dose escalation group) significantly increased (P=0.0132, Log-rank Mantel-Cox's test) the median of progression free survival in comparison to patients with Efavirenz plasma concentrations below 3000 ng/ml and no dose escalation (10 versus 3 months respectively).

DETAILED DESCRIPTION OF THE INVENTION

The present invention first concerns a method for treating cancer in a patient in need thereof, comprising administering to said patient a therapeutically efficient amount of Efavirenz, wherein said therapeutically efficient amount of Efavirenz generates an Efavirenz plasma concentration in said patient superior to 3000 ng/ml.

Similarly, the invention also concerns the use of Efavirenz, or a composition comprising Efavirenz and a pharmaceutically acceptable carrier, for treating cancer in a patient in need thereof, wherein Efavirenz is administered at a dose generating an Efavirenz plasma concentration in said patient superior to 3000 ng/ml.

The invention further concerns Efavirenz, or a composition comprising Efavirenz and a pharmaceutically acceptable carrier, for use in the treatment of cancer in a patient, wherein Efavirenz is administered to the patient at a dose generating an Efavirenz plasma concentration in said patient superior to 3000 ng/ml.

The invention also concerns the use of Efavirenz for preparing a medicament intended for the treatment of cancer in a patient, wherein Efavirenz is administered to the patient at a dose generating an Efavirenz plasma concentration in said patient superior to 3000 ng/ml.

The dose is preferably administered on a daily basis (daily dose).

Preferably, a suitable or optimal Efavirenz daily dose for the patient is determined based on Efavirenz plasma concentration monitoring.

By a "suitable" Efavirenz dose, it is meant an Efavirenz dose generating an Efavirenz plasma concentration of at least 3000 ng/ml. By an "optimal" Efavirenz dose, it is meant an Efavirenz dose generating an Efavirenz plasma concentration of at least 3000 ng/ml and no more than 10000 ng/ml. Indeed, while an Efavirenz plasma concentration of at least 3000 ng/ml is important for anticancer therapeutic efficiency and Efavirenz is generally well tolerated in human subjects, increasing the Efavirenz plasma concentration above 10000 ng/ml might potentially result in increased toxicity. An optimal Efavirenz dose thus generates an Efavirenz plasma concentration between 3000 ng/ml and 10000 ng/ml.

There is some inter-individual variability in the Efavirenz plasma concentrations obtained in distinct subjects based on a similar dose of Efavirenz. In particular, it is known in the art that subjects with loss or decrease of function mutations in both alleles of gene CYP2B6—which is the main gene involved in the metabolism and clearance of Efavirenz in vivo—have a slower metabolism of Efavirenz and reach much higher Efavirenz plasma concentrations than other subjects (Rotger, 2007). In addition to this specific case, additional inter-individual variability still exists, in particular based on the presence of a single loss or decrease of function allele in gene CYP2B6, or on the presence of one or two loss or decrease of function allele(s) in further genes involved in the metabolism and clearance of Efavirenz, such as CYP2A6 or UGT2B7 genes (Kwara, 2009a). Therefore, the simplest way to ascertain an Efavirenz plasma concentration of at least 3000 ng/ml is to monitor the Efavirenz plasma concentration obtained in each patient after administration of a specific dose of Efavirenz.

Monitoring of Efavirenz plasma concentration is preferably performed by measuring Efavirenz plasma concentration based on a plasma or blood sample taken from the patient. While Efavirenz clearance and thus plasma concentrations display an induction phase (up to 2 to 4 weeks of daily treatment) and a steady-state phase (after 4 weeks of daily treatment), Efavirenz clearance rate only lightly changes between the two phases, so that Efavirenz plasma concentration may be measured based on a sample taken at any time after Efavirenz treatment beginning. However, Efavirenz plasma concentration may preferably be measured as soon as a steady state Efavirenz plasma concentration has been attained. It is usually the case if the measure is made based on a plasma or blood sample taken at least about 10 days, for instance about 2 weeks, after starting daily administration of Efavirenz (Kappelhoff, 2005). In addition, due to the Efavirenz long half-life in vivo, Efavirenz plasma concentration only minimally varies during the 24 hours following daily intake, so that the measure of Efavirenz plasma concentration may be performed on a sample taken at any time after intake, in particular on a sample taken between 8 to 20 hours after a daily ingestion of Efavirenz (Marzolini, 2001).

The measure of Efavirenz plasma concentration may be made by any suitable technology known in the art, methods generally including a high performance liquid chromatography step, including but not limited to liquid chromatography coupled to tandem mass spectrometry (LC-MS/MS) (Ter Heine R, 2007; Villani P, 2001; Egge-Jacobsen W, 2004), a high performance liquid chromatography UV method (HPLC-UV) (Rezk N L, 2006; Takahashi, 2005; Marzolini, 2000).

While there is some inter-individual variability in Efavirenz plasma concentrations of subjects without 2 loss or decrease of function alleles for gene CYP2B6 involved in Efavirenz metabolism, such inter-individual variability is limited, compared to the huge increase in Efavirenz plasma concentrations that may be observed in subjects with two loss or decrease of function alleles for gene CYP2B6. Therefore, alternatively or in addition to Efavirenz plasma concentration monitoring, a suitable or optimal Efavirenz daily dose (as defined above) for the patient may also be determined based on genotyping of the patient's CYP2B6 alleles.

CYP2B6 alleles genotyping may be performed based on any suitable sample of the patient, such as a blood sample, which may further be used to measure Efavirenz plasma concentration.

CYP2B6 alleles genotyping may be performed by various methods well known to those skilled in the art, including sequencing (Rotger, 2007), amplification followed by real-time PCR allelic discrimination (Wyen, 2008), matrix-assisted laser desorption/ionization-time of flight mass spectrometry (Rotger, 2007), fluorometric 5' nuclease genotyping assays (Kwara, 2009b).

Loss or decrease of function alleles includes the alleles described in following Table 1, the nomenclature of which is in accordance with the CYP Allele Nomenclature Committee (http://www.cypalleles.ki.se).

TABLE 1

Main known loss or decrease of function CYP2B6 alleles

| Allele | Nucleotide change(s) in cDNA |
|---|---|
| CYP2B6*6 | 516G > T; 785A > G |
| CYP2B6*7 | 516G > T; 785A > G 1459C > T |
| CYP2B6*9 | 516G > T |
| CYP2B6*13 | 415A > G; 516G > T; 785A > G |
| CYP2B6*16 | 785A > G; 983T > C |
| CYP2B6*18 | 983T > C |
| CYP2B6*26 | 499C > G; 516G > T; 785A > G |
| CYP2B6*27 | 593T > C |
| CYP2B6*28 | 917C > G; 1132C > T |

With current commercially available Efavirenz formulations (such as Sustiva®), a daily Efavirenz dose of at least 1800 mg, in particular 1800 or 2200 mg, is suitable for generating an Efavirenz plasma concentration of at least 3000 ng/ml in a majority of subjects. Indeed, the inventors have determined that a daily dose between 1800 and 2200 mg of Efavirenz permits to generate an Efavirenz plasma concentration of at least 3000 ng/ml in a majority of patients, thus permitting to reach therapeutic efficiency in a majority of treated patients. As a result, in a preferred embodiment, the daily dose of Efavirenz administered to the patient is at least 1800 mg, in particular between 1800 and 2200 mg, such as 1800, 1900, 2000, 2100 or 2200 mg.

However, while a daily Efavirenz dose of at least 1800 mg, in particular between 1800 and 2200 mg (such as 1800, 1900, 2000, 2100 or 2200 mg), is generally necessary for generating an Efavirenz plasma concentration of at least 3000 ng/ml in subjects without two loss or decrease of function CYP2B6 alleles, a lower Efavirenz daily dose may be used in subjects with two loss or decrease of function CYP2B6 alleles. Preferably, a daily dose of at least 1800 mg, in particular between 1800 and 2200 mg (such as 1800, 1900, 2000, 2100 or 2200 mg), is thus administered to a patient without two loss or decrease of function CYP2B6 alleles. In contrast, for a patient with two loss or decrease of function CYP2B6 alleles, the daily dose of Efavirenz may be of 600 mg only, since this daily dose is generally sufficient to reach Efavirenz plasma concentrations of at least 3000 ng/ml (Rotger, 2007).

In addition, a lower Efavirenz daily dose might be possible with new Efavirenz formulation improving Efavirenz bioavailability in vivo. Indeed, the essential point is to reach an Efavirenz plasma concentration of 3000 ng/ml, no matter which is the dose of Efavirenz administered.

The invention also relates to a method for treating cancer in a patient in need thereof, comprising administering to said patient a therapeutically efficient amount of Efavirenz, wherein the daily dose of Efavirenz administered to the patient is at least 1800 mg, in particular between 1800 and 2200 mg, such as 1800, 1900, 2000, 2100 or 2200 mg. Similarly, the invention also concerns the use of Efavirenz, or a composition comprising Efavirenz and a pharmaceutically acceptable carrier, for treating cancer in a patient in need thereof, wherein Efavirenz is administered at a daily dose of at least 1800 mg, in particular between 1800 and 2200 mg, such as 1800, 1900, 2000, 2100 or 2200 mg. The invention further concerns Efavirenz, or a composition comprising Efavirenz and a pharmaceutically acceptable carrier, for use in the treatment of cancer in a patient, wherein Efavirenz is administered to the patient at a daily dose of at least 1800 mg, in particular between 1800 and 2200 mg, such as 1800, 1900, 2000, 2100 or 2200 mg.

The invention also concerns the use of Efavirenz for preparing a medicament intended for the treatment of cancer in a patient, wherein Efavirenz is administered to the patient at a daily dose of at least 1800 mg, in particular between 1800 and 2200 mg, such as 1800, 1900, 2000, 2100 or 2200 mg.

Indeed, the inventors have determined that a daily dose between 1800 and 2200 mg of Efavirenz permits to generate an Efavirenz plasma concentration of at least 3000 ng/ml in 84% of patients, thus permitting to reach therapeutic efficiency in a majority of treated patients.

In order to limit potential adverse effects, the Efavirenz daily dose should preferably be lower than 2500 mg, at least as a first administration daily dose. However, it may be possible to increase Efavirenz daily dose higher than 2500 mg in the context of Efavirenz daily dose adaptation (see below), when starting from a lower Efavirenz daily dose.

The present invention also relates to a method for treating cancer in a patient in need thereof, comprising:
  a) optionally, genotyping CYP2B6 alleles of said patient,
  b) administering a preliminary daily dose $D_P$ of Efavirenz to the patient,
  c) monitoring Efavirenz plasma concentration in the patient,
  d) administering an optimized daily dose $D_O$ of Efavirenz to the patient, wherein:
    i) if the patient's Efavirenz plasma concentration is inferior to 3000 ng/ml, then the optimized daily dose $D_O$ of Efavirenz is increased compared to the preliminary daily dose $D_P$,
    ii) if the patient's Efavirenz plasma concentration is superior to 3000 ng/ml, then the optimized daily dose $D_O$ of Efavirenz is the same as or lower than the preliminary daily dose $D_P$.

Similarly, the invention also concerns the use of Efavirenz, or a composition comprising Efavirenz and a pharmaceutically acceptable carrier, for treating cancer in a patient in need thereof, wherein Efavirenz dose is optimized by:
  a) optionally, genotyping CYP2B6 alleles of said patient,
  b) administering a preliminary daily dose $D_P$ of Efavirenz to the patient,
  c) monitoring Efavirenz plasma concentration in the patient,
  d) administering an optimized daily dose $D_O$ of Efavirenz to the patient, wherein:
    i) if the patient's Efavirenz plasma concentration is inferior to 3000 ng/ml, then the optimized daily dose $D_O$ of Efavirenz is increased compared to the preliminary daily dose $D_P$,
    ii) if the patient's Efavirenz plasma concentration is superior to 3000 ng/ml, then the optimized daily dose $D_O$ of Efavirenz is the same as or lower than the preliminary daily dose $D_P$.

The invention further concerns Efavirenz, or a composition comprising Efavirenz and a pharmaceutically acceptable carrier, for use in the treatment of cancer in a patient, wherein Efavirenz dose is optimized by:
  a) optionally, genotyping CYP2B6 alleles of said patient from a patient's sample,
  c) measuring Efavirenz plasma concentration in a blood or plasma sample of the patient to which a preliminary daily dose $D_P$ of Efavirenz has been administered,
  d) determining an optimized daily dose $D_O$ of Efavirenz to the patient, wherein:
    i) if the patient's Efavirenz plasma concentration is inferior to 3000 ng/ml, then the optimized daily dose $D_O$ of Efavirenz is increased compared to the preliminary daily dose $D_P$,
    ii) if the patient's Efavirenz plasma concentration is superior to 3000 ng/ml, then the optimized daily dose $D_O$ of Efavirenz is the same as or lower than the preliminary daily dose $D_P$.

The invention also concerns the use of Efavirenz for preparing a medicament intended for the treatment of cancer in a patient, wherein Efavirenz dose is optimized by:
  a) optionally, genotyping CYP2B6 alleles of said patient from a patient's sample,
  c) measuring Efavirenz plasma concentration in a blood or plasma sample of the patient to which a preliminary daily dose $D_P$ of Efavirenz has been administered,
  d) determining an optimized daily dose $D_O$ of Efavirenz to the patient, wherein:
    i) if the patient's Efavirenz plasma concentration is inferior to 3000 ng/ml, then the optimized daily dose $D_O$ of Efavirenz is increased compared to the preliminary daily dose $D_P$,
    ii) if the patient's Efavirenz plasma concentration is superior to 3000 ng/ml, then the optimized daily dose $D_O$ of Efavirenz is the same as or lower than the preliminary daily dose $D_P$.

In a preferred embodiment of the above method of treatment involving Efavirenz dose adaptation based on Efavirenz plasma concentration monitoring, the preliminary daily dose $D_P$ of Efavirenz administered to the patient is 1800 mg, because the inventors have determined that a daily dose of 1800 mg of Efavirenz permits to generate a mean Efavirenz plasma concentration superior to 3000 ng/ml, thus permitting to reach therapeutic efficiency in a majority of treated patients. Alternatively, a lower preliminary daily dose $D_P$ of Efavirenz may be administered to the patient, such as 600 or 1200 mg for instance. Optionally, if CYP2B6 alleles have been genotyped and the patient has two loss or decrease of function CYP2B6 alleles, then the preliminary daily dose $D_P$ of Efavirenz administered to the patient may be lower, such as 600 mg.

The measure of Efavirenz plasma concentration may be made based on a sample taken from the patient at any suitable time after administration of a preliminary Efavirenz daily dose $D_P$, as described above, in particular at least about 10 days (for instance about 2 weeks) after starting Efavirenz daily administration.

After measuring of Efavirenz plasma concentration, the Efavirenz daily dose is optimized, with the following rules:
  i) if the patient's Efavirenz plasma concentration is inferior to 3000 ng/ml, then the optimized daily dose $D_O$ of Efavirenz is increased compared to the preliminary daily dose $D_P$.
  Depending on the measured Efavirenz plasma concentration, the Efavirenz daily dose may be more or less increased.
  Those skilled in the art would know how to increase of Efavirenz daily dose. In particular, if the measured Efavirenz plasma concentration is close to 3000 ng/ml (for example 2000-3000 ng/ml), then the Efavirenz daily dose is only slightly increased, for example an increase of 10-50% compared to the preliminary daily dose $D_P$. If the preliminary daily dose $D_P$ of Efavirenz administered to the patient is 1200 mg, the optimized Efavirenz daily dose $D_O$ may then be for instance 1400 mg (about 17% increase), 1600 mg (about 33% increase), or 1800 mg (50% increase).

In contrast, if the measured Efavirenz plasma concentration is significantly lower than 3000 ng/ml (for example <2000 ng/ml), then the Efavirenz daily dose is more significantly increased, for instance an increase of 50-100% compared to the preliminary daily dose $D_P$. If the preliminary daily dose $D_P$ of Efavirenz administered to the patient is 1200 mg, the optimized Efavirenz daily dose $D_O$ may then be for instance 1800 mg (50% increase), 2000 mg (about 67% increase), 2200 mg (about 83% increase), or 2400 mg (100% increase).

ii) if the patient's Efavirenz plasma concentration is superior to 3000 ng/ml, then the optimized daily dose $D_O$ of Efavirenz is the same as or lower than the preliminary daily dose $D_P$.

Depending on the measured Efavirenz plasma concentration, the Efavirenz daily dose may be the same as or lower than the preliminary daily dose $D_P$.

If the measured Efavirenz plasma concentration is not much higher than 3000 ng/ml (for example 3000-5000 ng/ml), the optimized Efavirenz daily dose $D_O$ may be the same as the preliminary daily dose $D_P$.

If the measured Efavirenz plasma concentration is much higher 3000 ng/ml (for example >5000 ng/ml), the optimized Efavirenz daily dose $D_O$ may also be the same as the preliminary daily dose $D_P$ but might preferably be lower than the preliminary daily dose $D_P$, in order to prevent potential adverse effects. Those skilled in the art would know how to decrease of Efavirenz daily dose. For instance, an example in the treatment of HIV infection is described in Fayet Mello, 2011. In particular, if the Efavirenz plasma concentration is >10 000 ng/ml, the optimized Efavirenz daily dose $D_O$ will preferably be lower than the preliminary daily dose $D_P$.

In the above methods, uses or compositions involving an optimization of Efavirenz daily dose based on measured Efavirenz plasma concentration, steps c) (measure of Efavirenz plasma concentration) and d) (optimization of the Efavirenz daily dose) may be repeated if necessary or useful.

The methods of treatment, uses or compositions according to the invention are applicable to any type of cancer in which L1-RT is expressed or overexpressed. Indeed, dedifferentiation, epithelial-mesenchymal transition (EMT) and resistance to apoptosis play an important role in pathophysiology of several types of cancers, and Efavirenz has been shown to antagonize all those mechanisms of cancer progression. It has been shown that L1-RT is particularly overexpressed in epithelial cancers (Lee, 2012). By "epithelial cancer" or "carcinoma", it is meant any malignant neoplasm originating from epithelium or related tissues that develop in the skin, hollow viscera and other organs. Therefore, in a preferred embodiment, the patient treated with Efavirenz in an amount generating an Efavirenz plasma concentration in said patient superior to 3000 ng/ml is suffering from an epithelial cancer, in particular but not limited to from prostate cancer, lung cancer, ovarian cancer, colorectal cancer, or melanoma. In a particularly preferred embodiment, the patient is suffering from prostate cancer, in particular from hormone refractory prostate cancer, including androgen-independent hormone refractory prostate cancer.

While the methods, uses or compositions according to the invention may be used in any (preferably human) patient suffering from any type of cancer, it is more particularly intended for patients who are not also infected by human immunodeficiency virus (HIV). However, it may also be used for HIV-infected individuals suffering at the same time of a cancer. The Efavirenz dose is then simply adapted in order to be efficient on cancer cells.

The present invention also relates to a unique dosage form of Efavirenz, comprising Efavirenz in an amount generating an Efavirenz plasma concentration in said patient superior to 3000 ng/ml upon administration of at most two (i.e. one or two) units of said unique dosage form, and a pharmaceutically acceptable carrier.

When only one unit of said unique dosage form of Efavirenz is able to generate upon administration to a patient an Efavirenz plasma concentration in said patient superior to 3000 ng/ml, the Efavirenz amount in said unique dosage form is preferably superior or equal to 1800 mg, and may preferably be between 1800 and 2200 mg, such as 1800, 1900, 2000, 2100 or 2200 mg. Alternatively, when the unique dosage form of Efavirenz is designed so that a plasma Efavirenz concentration of at least 3000 ng/ml is obtained in most patients by administration of two units of the unique dosage form, the Efavirenz amount in said unique dosage form is preferably superior or equal to 900 mg, in particular between 900 and 1100 mg, such as 900, 950, 1000, 1050 or 1100 mg. Indeed, the inventors have determined that a daily dose of 1800 mg of Efavirenz permits to generate a mean of Efavirenz plasma concentration >3500 ng/ml and a daily dose of 2200 mg of Efavirenz permits to generate a mean of Efavirenz plasma concentration >6500 ng/ml. Any usual pharmaceutically acceptable carrier may be used, including one or more of sodium laurylsulfate, monohydrated lactose, magnesium stearate, sodium carboxymethylstarch.

Such a unique dosage form of Efavirenz may be in any appropriate form, such as in the form of a tablet, a capsule, a powder, or granules.

Example 1

Choice of the Dose of Efavirenz to Treat Hormone Refractory-Prostate Cancer

Efavirenz (see formula in FIG. 1) is a benzoxazinone and is a particularly well tolerated molecule and used for the treatment of AIDS at the daily dosage of 600 mg/day. Data obtained in humans treated with 600 mg/day of Efavirenz show that plasma concentrations above 1500 ng/ml are observed in approximately 70-80% (Marzolini, 2001) of the subjects.

It has been shown in rats treated with Efavirenz (WO03555493) that tumor progression is inhibited for a dose of approximately 5 mg/kg/day (1 mg/rat/day intraperitoneally, weight of one rat approximately 200 g). In parallel, a pharmacokinetic study in rats published by Balani et al (1999) has shown that an intravenous injection of 5 mg/kg of Efavirenz gives a maximal plasma concentration of the drug of 5 µM, corresponding to 1578 ng/ml.

The daily dosage of 600 mg/day of Efavirenz used for the treatment of AIDS could thus reasonably be expected to be also efficient for the treatment of cancer in humans.

A clinical trial (FAVE study) of the use of Efavirenz in the treatment of hormone-refractory prostate cancer was thus launched based on a dose of Efavirenz of 600 mg/day.

Later, another clinical trial (ESCALE study) was further launched. This study allowed to determine the daily doses of Efavirenz that will ensure plasma level of Efavirenz >3000 ng/ml in a majority of patients.

Fave Study
I. Trial Synopsis
1. Trial Rationale

Prostate cancer progression is initially well controlled by first generation hormone therapies. However, after few years, hormone-resistance develops and androgen blockade is no longer efficient. At this stage, the most used marker of cancer progression is the raise in plasma level of the protein PSA. When PSA raises, the patient is still asymptomatic and no treatment is recommended. After six to twelve months, the patient becomes symptomatic and chemotherapy is implemented (taxotere). This asymptomatic period (six to twelve months) is a very good window to test in monotherapy a new drug devoid of significant side effects, such as Efavirenz. In this context, the primary endpoint is usually the stabilization of PSA level associated with other measures of cancer progression such as the appearance of new metastasis and clinical symptoms.

2. Target Population and Study Objectives

The patients included in the FAVE study had a metastatic hormone-refractory prostate cancer without any clinical symptoms related to disease progression and raising serum PSA, despite a serum testosterone under 50 ng/dl. The primary objective of this study was to assess the effect of Efavirenz on PSA progression at 3 months. For the exploratory analysis, following the latest recommendations of the Prostate Cancer Clinical Trials Working Group (Scher, 2008), PSA progression was defined as an increase of more than 25% over the baseline and an increase in the concentrations of PSA of at least 2 ng/ml. The clinical symptoms, the number of new bone metastasis and the global response to treatment (evaluated by the RECIST criteria) were also recorded. After three months, the global response and the overall survival were evaluated in a follow up study.

Patients received 600 mg of Efavirenz per day and, during Efavirenz treatment, hormone therapy was maintained. This dose was chosen because it corresponds to the dose used for the treatment of HIV and as described above was predicted to be efficacious for cancer treatment in 70-80% of the studied population. However, it is difficult to predict precisely the efficacious dose in humans based on preclinical data. For this reason, the goal of the FAVE study was twofold: 1. To demonstrate the clinical efficacy and 2. Explore the relationship between the dose of the compound and clinical efficacy.

In order to establish the minimal efficacious dose that could be effective for the treatment of prostate cancer the inventor used a correlational approach in which plasma concentrations of Efavirenz were related to treatment efficacy measured at the three month time point.

This approach was followed by an interventional approach aimed to establish a causal relationship between dose and efficacy of the treatment. In this case after three months of treatment at the 600 mg/day dose, the doses of Efavirenz were progressively raised to reach 1.2 g/day.

Sixty-one patients were included in the study and fifty-three patients had no violation of the eligibility criteria and received Efavirenz at least once (general population). The assessment of Efavirenz plasma concentrations was an optional exploratory objective to which the patients had to expressly consent. Plasma Efavirenz concentrations at the three month time point were available for 41 patients that were used for the exploratory analysis.

3. Study Centers

The FAVE study was performed in five study centers: 1. Institut Claudius Regaud (Toulouse); 2. Institut Francois Baclesse (Caen); 3. Institut Antoine Lacassagne (Nice); 4. Centre Hospitalier Departemental—Les Oudaires (La Roche sur Yon); 5. Institut Bergonié (Bordeaux) that also acted as sponsor and coordinator of the study.

II. Evaluation of Plasma Efavirenz Concentration
Blood Samples

Blood samples for the evaluation of Efavirenz plasma concentrations were taken at three months after the start of Efavirenz treatment. For Efavirenz plasma concentration determination, 10 ml of blood were collected using sodium or lithium heparinate tubes. After each blood collection, the tubes of blood were centrifuged for 5 minutes at 5000 g. Plasma was collected in polypropylene tubes. The plasma tubes of each subject were packed and stored in appropriately labelled plastic frost-resistant bags and stored at −20° C. until analysis.

Samples were sent to a pharmacokinetic analysis laboratory for Efavirenz concentration analysis that was performed using a validated mass-spectrometry coupled to liquid chromatography (UPLC-MS/MS) method.

Extraction Procedure

20 µL of internal standard solution (Efavirenz $^{13}$C à 2 µg/mL in methanol) and 300 µL of Potassium Hydroxide Buffer (0.01 M) were added to 150 µL of plasma sample. The sample was vortex-mixed for 30 sec, and then 5 mL of diethyl ether was added. After 15 min under agitation, the organic and aqueous phases were separated by centrifugation at 3000 rpm for 10 min. The upper organic phase was transferred to a glass tube and evaporated at room temperature under a stream of nitrogen. The residue was re-dissolved in 150 µL of methanol.

Liquid Chromatography/Mass Spectrometry

The UPLC-MS/MS unit consisted of Waters ACQUITY UPLC® instrument coupled with an Acquity TQD® detector. Separations were performed at 40° C. on an Acquity UPLC® BEH C18 column (50*2.1 mm) at a flow rate of 0.3 mL/min. Gradient elution was performed over 2.3 minutes using a combination of acetonitrile and ammonium formate buffer (4 mM) as mobile phase. Detections were performed with electrospray ionization (ESI) in negative ion mode. The mass spectrometer was operated in the multiple-reaction monitoring (MRM) mode. The selected ion transitions used for the quantification and confirmation were 314.3→69 and 314.3→244 respectively. Calibration curves were obtained by analysis of standard solutions prepared in plasma in the range 100-10000 ng/mL and limit of quantification (LOQ) was 2.5 ng/mL.

III. Results of the Study
1. Assay Results at the Three Month Time Point

The analysis of the effects of Efavirenz in the population of patients that received 600 mg/day of Efavirenz (N=53) indicates that a total of 15/53 (28%) showed non-progressions for PSA levels at 3 months, whilst in 72% of patients the disease continued to progress. These results do not allow then to claim clinical efficacy of Efavirenz for the treatment of prostate cancer at the 600 mg dose.

Figure 2:
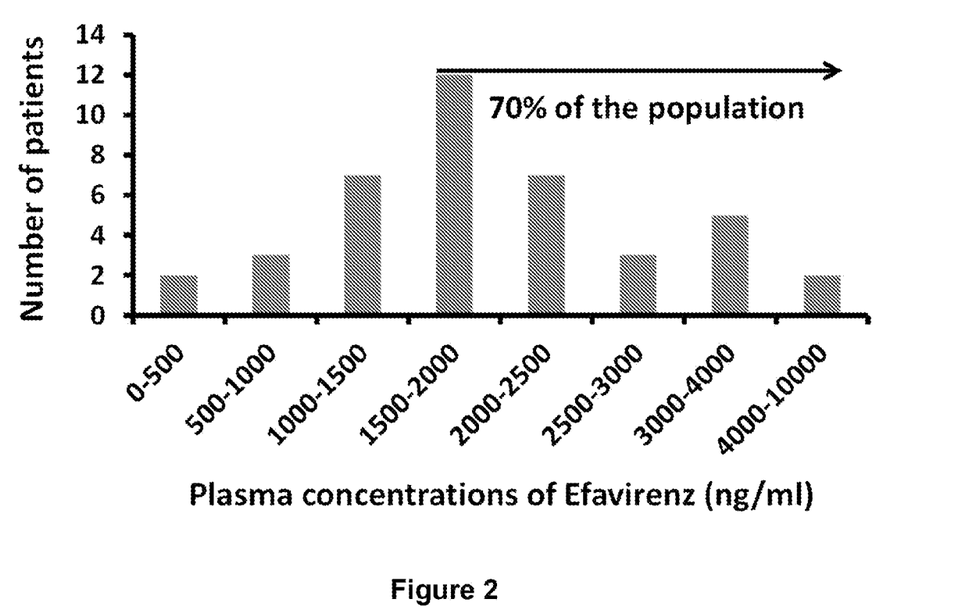
FIG. 2: Distribution of the plasma concentrations of Efavirenz in patients of the FAVE study. 70% of the patients had plasma concentrations of Efavirenz >1500 ng/ml.

This result was surprising since the plasma concentration of Efavirenz in the 41 patients of the study for which plasma concentrations of Efavirenz were available showed that the threshold dose (≥1500 ng/ml) was observed in 70% of the treated patients (see FIG. 2). Consequently, despite expected Efavirenz plasma concentrations were found in patients treated with 600 mg/day, this dose was not efficient to treat cancer.

We then evaluated if higher doses of Efavirenz were necessary for the treatment of prostate cancer. At this purpose, we first analyzed if plasma concentrations of Efavirenz were related to treatment efficacy. This analysis was conducted on the 41 patients for whom plasma Efavirenz concentrations were available.

Figure 3:
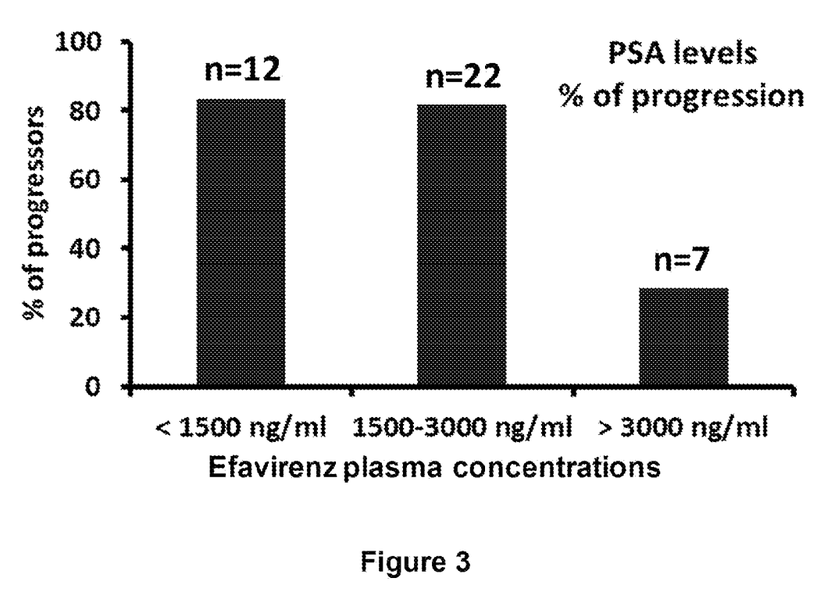
FIG. 3: Three months of Efavirenz treatment (600 mg/day) improved the evolution of hormone refractory prostate cancer as a function of the plasma concentrations of the drug. The patients with the highest plasma concentrations of Efavirenz (>3000 ng/ml) had the lowest PSA progression [>3000 versus <1500: P=0.0449 (two tailed) and P=0.029 (one tailed); >3000 versus 1500-3000: P=0.0164 (two and one tailed), Fisher's exact test].

Patients (N=41) were divided in three groups depending on their plasma concentrations of Efavirenz (<1500 ng/ml, N=12; 1500-3000 ng/ml, N=22; >3000 ng/ml, N=7). A clear concentration-response effect was observed (see FIG. 3). In the group with Efavirenz concentrations above 3000 ng/ml, PSA progression (FIG. 3A) was observed in only 28.6% of the subjects (71.4% of non-progressors). In contrast, in patients with low and intermediate plasma concentrations of Efavirenz (<1500 ng/ml and 1500-3000 ng/ml groups), PSA progressed in 83.3% and 81.8% of the subjects respectively [>3000 versus <1500: P=0.0449 (two tailed) and P=0.029 (one tailed); >3000 versus 1500-3000 P=0.0164 (two and one tailed), Fisher's exact test]. The groups with low and intermediated concentrations of Efavirenz did not differ significantly for the percentage of progression of both PSA levels [P=1 (two-tailed) and P=0.649 (one tailed) Fisher's exact test].

In conclusion, the results obtained at the three month time point suggest that Efavirenz is effective for the treatment of hormone refractory prostate cancer when plasma concentration superior at 3000 ng/ml are reached. As a consequence, doses higher than 600 mg/day have to be used in order to obtain a relevant effect in a significant proportion of the patients.

2. Results of the Follow Up Study

Figure 4:
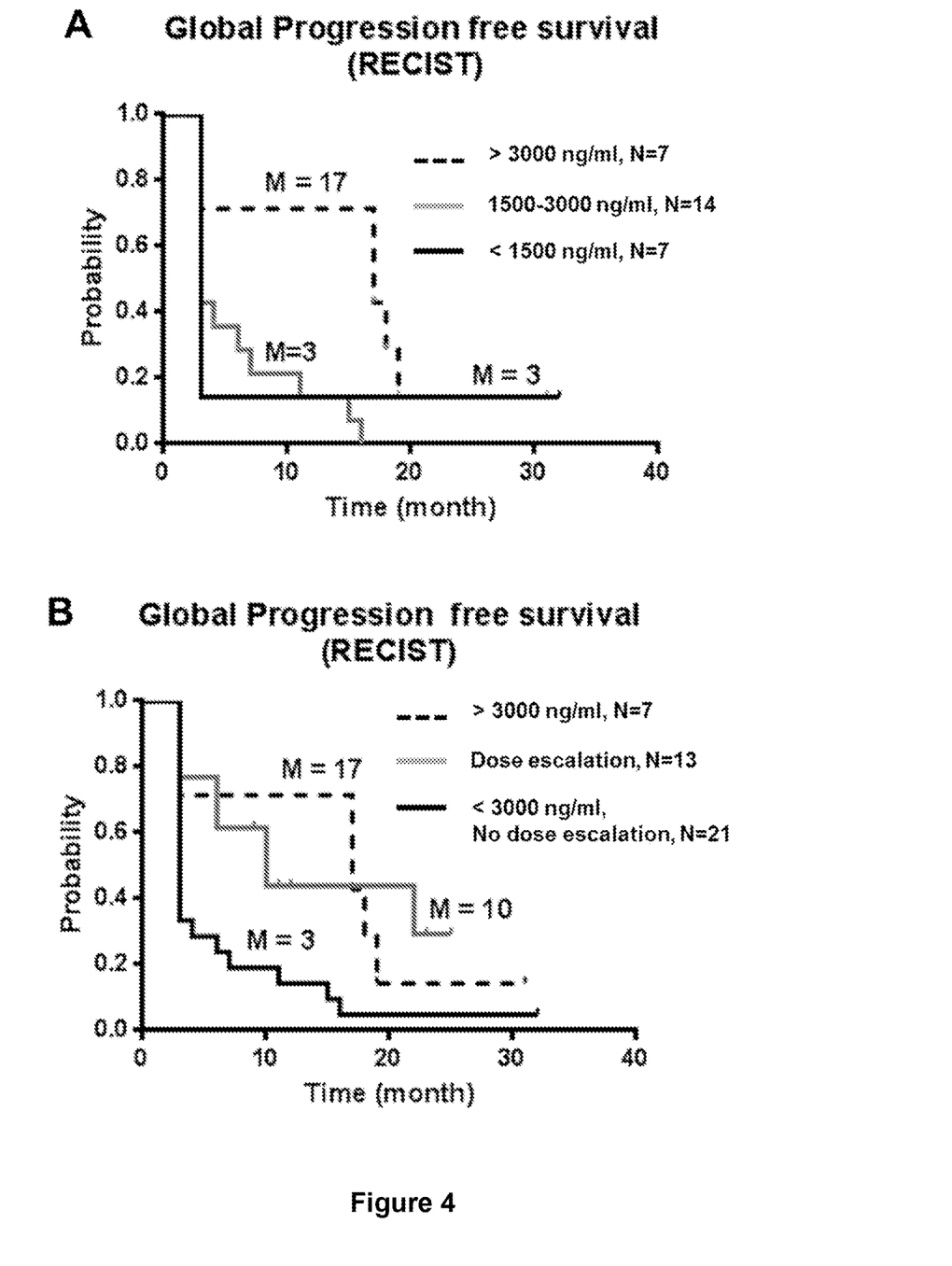

Differences in disease progression as a function of plasma Efavirenz concentrations were confirmed in the follow up study. FIG. 4A shows an intention to treat (ITT) analysis of the progression free survival, measured using the RECIST criteria, in the <1500 ng/ml, 1500-3000 ng/ml and >3000 ng/ml plasma concentrations of Efavirenz groups. As observed at the three months analysis, the low (<1500 ng/ml) and intermediate (1500-3000 ng/ml) Efavirenz groups did not differ significantly (P=0.8602, Log-rank Mantel-Cox's test) and had a shorter disease progression free survival (Median=3 months for both groups) than the >3000 ng/ml Efavirenz group (Median=17 months) (P=0.0182; Log-rank Mantel-Cox's test, the <1500 and 1500-3000 groups were cumulated for statistical analysis).

In order to establish a causal relationship between the dose and treatment efficacy during the follow up period, the investigators increased the daily dose of Efavirenz (up to 1200 mg/day) in thirteen patients which originally had low Efavirenz plasma concentrations (<3000 ng/ml). These thirteen patients were used to constitute the dose escalation group. When an ITT analysis was performed, the increase in dose of Efavirenz in the dose escalation group (FIG. 4B) significantly increased (P=0.0132, Log-rank Mantel-Cox's test) the median of progression free survival (Median=10 months) in comparison to patients (Median=3 months) with low plasma Efavirenz concentrations (<3000 ng/ml group) that did not receive a dose escalation. A significant difference (P=0.0182, Log-rank Mantel-Cox's test) was also found when patients in the high Efavirenz concentrations group (>3000 ng/ml) were compared with patients with low Efavirenz concentrations and no dose escalation (<3000 ng/ml group).

Figure 5:
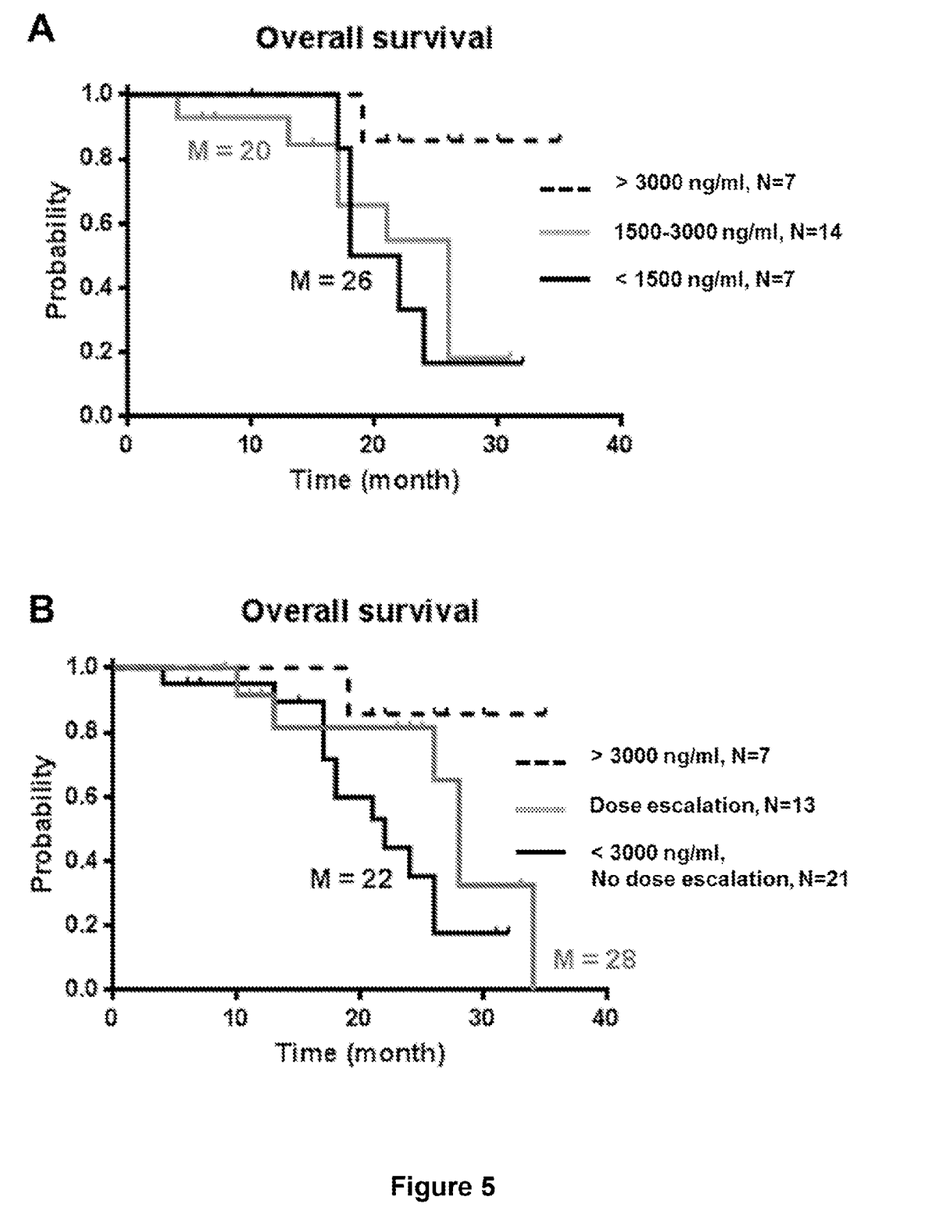
FIG. 5: Intention to treat (ITT) analysis of the overall survival (OS) of hormone refractory prostate cancer patients as a function of Efavirenz plasma concentrations (A) and in patient in the dose escalation group (B). Overall survival was highest in the patient with the higher plasma concentration of Efavirenz (>3000 ng/ml) and was increased in the patient receiving a dose escalation (dose escalation group) compared with the patient that remained at 600 mg of Efavirenz (No dose escalation).

To further test the influence of Efavirenz plasma concentrations on disease progression, we also evaluated the Overall Survival (OS). As observed for the Progression Free Survival the OS was superior in the patient with Efavirenz plasma concentrations>3000 ng/ml than in the other two groups (<1500 ng/ml, 1500-3000 ng/ml) (FIG. 5A). Also in the dose escalation group the OS was increased in comparison to the low Efavirenz concentration group but was lower than in the >3000 ng/ml (FIG. 5B).

3. Conclusions

The results of the FAVE study in which Efavirenz was tested as a treatment of hormone-refractory prostate cancer show that the dose of 600 mg/day, effective for the treatment of HIV, is not effective to treat prostate cancer. In the case of cancer, Efavirenz plasmatic concentration has to reach at least 3000 ng/ml and the daily dose has to be superior to 600 mg/day, as shown by the increase in therapeutic efficacy observed with 1200 mg/day.

Escale Study

Following the results of FAVE study, that showed a higher therapeutic efficacy in the patient with at least 3000 ng/ml of Efavirenz in plasma compared with the patient with less than 3000 ng/ml of Efavirenz in plasma, another clinical study (ESCALE) was used to establish the daily doses of Efavirenz that will ensure plasma level of Efavirenz >3000 ng/ml in a majority of patients.

Trial Synopsis

The goal of ESCALE study is to test a dose of Efavirenz above 600 mg/day in cancer patients to evaluate the maximum tolerated dose (MTD) in order to obtain a better therapeutic effect. The clinical study ESCALE is ongoing.

1. Trial Summary

The ESCALE clinical study is a single arm, single center (Bergonie Institute), and dose escalation phase I study. Objectives of this study are to assess the safety, tolerability, and recommended dose of Efavirenz administered orally, by continuous once-daily administration in patients with solid tumors (no pancreatic cancer) and Non-Hodgkin Lymphoma (NHL) who have failed chemotherapy treatment. The scheme of the study is a dose escalation evaluated by continual reassessment method likelihood approach (O'Quickley, 1996). Initially, there were 6 dosing levels scheduled starting at 600 mg, day and up to a maximum of 3000 mg day of Efavirenz. The maximal subject number assessable is 30 patients.

2. Study Objectives

The primary objective is to evaluate the maximum tolerated dose (MTD) of Efavirenz that can be given in patients with refractory solid tumors or Non-Hodgkin Lymphoma using the National Cancer Institute Common Terminology for Adverse Events V4.0 (NCI-CTCAE V4.0). Dose limiting toxicities (DLT) are evaluated after 28 days (+/−7 days) of Efavirenz treatment.

There are 3 secondary objectives: the first one is to measure the pharmacokinetic profile of Efavirenz at 2, 4 and 12 weeks, the second one is to assess the objective response at 3 month and the last one is to evaluate the progression free survival (PFS) at 6 month for all the solid tumors (based on RECIST V1.1, Eisenhauer, 2009) and NHL (based on Cheson B D, 1999). In case of prostate cancer, time to biological progression at 6 month is evaluated according to Scher recommendation (Scher, J C O 2008).

Evaluation of Plasma Concentration of Efavirenz

1. Blood Samples

Blood samples for the evaluation of Efavirenz plasma concentrations were taken at 14 days, 28 days after the start of Efavirenz treatment. For Efavirenz plasma concentration determination, 10 ml of blood were collected using sodium or lithium heparinate tubes. After each blood collection, the tubes of blood were centrifuged for 5 minutes at 5000 g. Plasma was collected in polypropylene tubes. The plasma tubes of each subject were packed and stored in appropriately labelled plastic frost-resistant bags and stored at −20° C. until analysis.

Samples were sent to a pharmacokinetic analysis laboratory for Efavirenz concentration analysis that was performed using a validated mass-spectrometry coupled to liquid chromatography (UPLC-MS/MS) method.

2. Extraction Procedure

20 μL of internal standard solution (Efavirenz $^{13}$C à 2 μg/mL in methanol) and 300 μL of Potassium Hydroxide Buffer (0.01 M) were added to 150 μL of plasma sample. The sample was vortex-mixed for 30 sec, and then 5 mL of diethyl ether was added. After 15 min under agitation, the organic and aqueous phases were separated by centrifugation at 3000 rpm for 10 min. The upper organic phase was transferred to a glass tube and evaporated at room temperature under a stream of nitrogen. The residue was re-dissolved in 150 μL of methanol.

3. Liquid Chromatography/Mass Spectrometry

The UPLC-MS/MS unit consisted of Waters ACQUITY UPLC® instrument coupled with an Acquity TQD® detector. Separations were performed at 40° C. on an Acquity UPLC® BEH C18 column (50*2.1 mm) at a flow rate of 0.3 mL/min. Gradient elution was performed over 2.3 minutes using a combination of acetonitrile and ammonium formate buffer (4 mM) as mobile phase. Detections were performed with electrospray ionization (ESI) in negative ion mode. The mass spectrometer was operated in the multiple-reaction monitoring (MRM) mode. The selected ion transitions used for the quantification and confirmation were 314.3→69 and 314.3→244 respectively. Calibration curves were obtained by analysis of standard solutions prepared in plasma in the range 100-10000 ng/mL and limit of quantification (LOQ) was 2.5 ng/mL.

Figure 6:
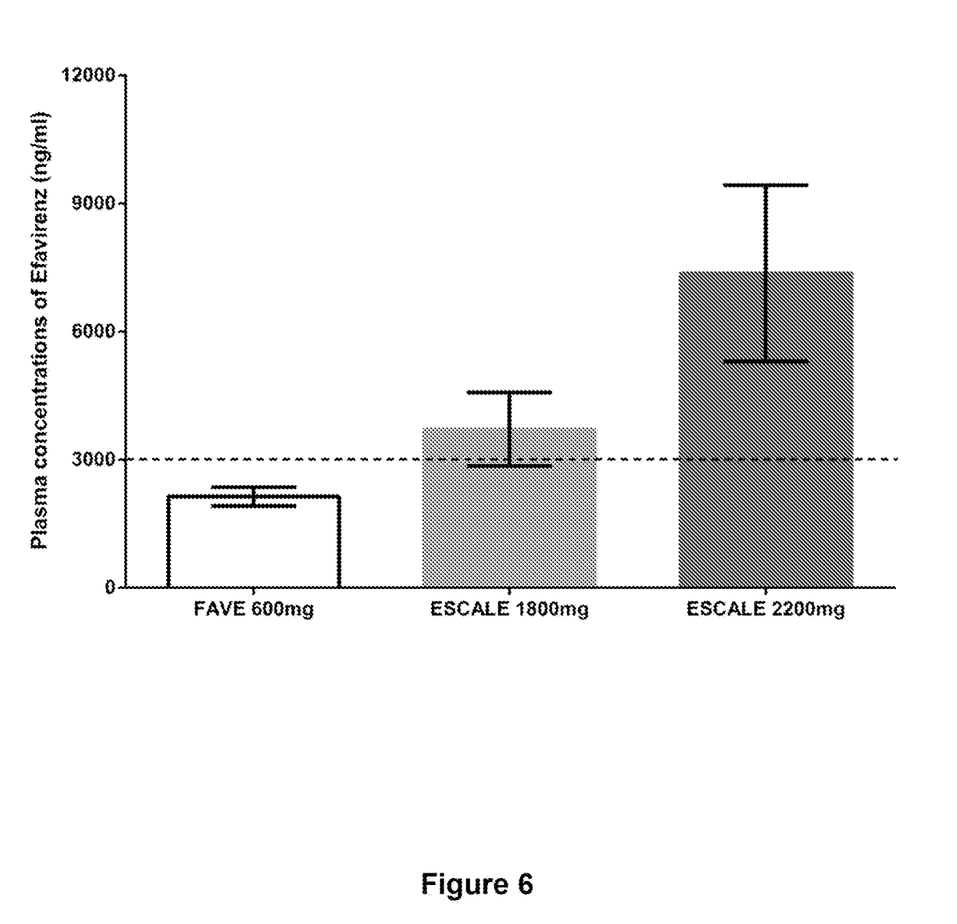
FIG. 6: Plasma concentration of Efavirenz (Mean±SEM) in cancer patient depending on the daily dose of Efavirenz 600, 1800 and 2220 mg.

Results of Plasma Efavirenz Concentration Assessment Depending on Efavirenz Daily Dose FIG. 6 shows results of Efavirenz plasma concentrations measured in patients receiving the dose of 1800 mg and 2200 mg/day (three patients per dose). These results were compared with the ones of the FAVE study in which the patient received 600 mg/day of Efavirenz. The mean plasma concentration of Efavirenz (2136 ng/ml) were below the therapeutic threshold (3000 ng/ml) in the patients receiving 600 mg/day and above the therapeutic threshold in patient receiving 1800 mg (3712 ng/ml) and 2200 mg (7364 ng/ml) of Efavirenz. Thus a dose equal or superior to 1800 mg of Efavirenz allows reaching therapeutic concentrations for the treatment of cancer in a majority of patients.

BIBLIOGRAPHIC REFERENCES

Ashworth A, et al. EMBO J. 1990 May; 9(5):1529-34
Babich V, et al. Gene. 1999 Nov. 1; 239(2):341-9.
Balani S K, et al. Drug Metab Dispos. 1999 January; 27(1):41-5.
Cheason B D et al, JCO 25(5)1999: 579-586.
Cho N Y, et al. J Pathol. 2007 February; 211(3):269-77
Cordaux R, et al. Nat Rev Genet. 2009 October; 10(10): 691-703. Review
Doucet A J, et al. PLoS Genet. 2010 October 7; 6(10). pii: e1001150.
Egge-Jacobsen W, et al. Ther Drug Monit 2004. October; 26(5):546-62.
Eisenhauer E A et al, EJC 45, 2009: 228-245
Estecio M R, et al. PLoS One. 2007 May 2; 2(5):e399
Fayet Mello A, et al. Antivir Ther. 2011; 16(2):189-97.
Ferrigno O, et al. Nat Genet. 2001 May; 28(1):77-81.
Feuchter-Murthy A E, et al. Nucleic Acids Res. 1993 Jan. 11; 21(1):135-43.
Gasior S L, et al. Gene. 2007 Apr. 1; 390(1-2):190-8. Epub 2006 Sep. 12
Gilbert N, et al. Mol Cell Biol. 2005 September; 25(17): 7780-95.
Goodier J L, et al. Cell. 2008 Oct. 3; 135(1):23-35. Review
Han J S, Szak et al. Nature. 2004 May 20; 429(6989):268-74.
Islam T C, et al. J Biol Chem. 1993 Feb. 15; 268(5):3251-9.
Kappelhoff B F, et al. 2005. Antiviral Therapy 10:489-498.
Kazazian H H Jr. Curr Opin Genet Dev. 1998 June; 8(3): 343-50. Review
Kwara A, et al. AIDS. 2009 Oct. 23; 23(16):2101-6. (a)
Kwara A, et al. Br J Clin Pharmacol 2009; 67:427-436. (b)
Lee E, et al. Science. 2012 Aug. 24; 337(6097):967-71.
Lin C, et al. Cell. 2009 Dec. 11; 139(6):1069-83. Epub
Mangiacasale et al. Oncogene. 2003 May 8; 22(18):2750-61.
Marzolini C, et al. J Chromatogr B. 2000, 740:43±58.
Marzolini C, et al. AIDS. 2001 Jan. 5; 15(1):71-5.
Nekrutenko A, et al. Trends Genet. 2001 November; 17(11): 619-21.
Neuhausen A, et al. Cancer Biol Ther. 2006 August; 5(8): 993-1001. Epub 2006 Aug. 4.
Norris J, et al. J Biol Chem. 1995 Sep. 29; 270(39):22777-82.
O'Quickley J et al. Biometrics, 1996
Pattamadilok J, et al. Int J Gynecol Cancer. 2008 July-August; 18(4):711-7. Epub 2007 Oct. 18
Rezk N L, et al. Ther Drug Monit. 2006 August; 28(4):517-25.
Roman-Gomez J, et al. Oncogene. 2005 Nov. 3; 24(48): 7213-23.
Rotger M et al. Clin Pharmacol Ther. 2007 April; 81(4): 557-66
Scher H I, et al. J Clin Oncol. 2008 Mar. 1; 26(7):1148-59.
Schulz W A, et al. Curr Top Microbiol Immunol. 2006; 310:211-50
Shaffer D R, et al. Nat Med. 2006 January; 12(1):14-5.
Sinibaldi-Vallebona P, et al. Genes Chromosomes Cancer. 2006 January; 45(1):1-10. Review.
Speek M. Mol Cell Biol. 2001 March; 21(6):1973-85.
Takahashi M, et al. Biol. Pharm. Bull. 2005. 28(7) 1286-1290.
Tangkijvanich P, et al. Clin Chim Acta. 2007 April; 379(1-2):127-33. Epub 2007 Jan. 19
Ter Heine R, et al. Rapid Commun Mass Spectrom. 2007; 21(15):2505-14.
Tomilin N V. Int Rev Cytol. 1999; 186:1-48. Review.
Tomlins S A, et al. Science. 2005 Oct. 28; 310(5748):644-8.
van Luin M, et al. Antivir Ther. 2009; 14(1):75-83.
Veldkamp A I, et al. The Journal of Infectious Diseases 2001; 184:37-42.
Villani P, et al. Ther Drug Monit 2001 August; 23(4):380-8.
Whitelaw E, et al. Nat Genet. 2001 April; 27(4):361-5.
WO03055493A1.
WO2006069812A2.
Wyen, C, et al. J Antimicrob Chemother. 2008 April; 61(4): 914-8. Epub 2008 Feb. 14.

The invention claimed is:

1. A method for treating prostate cancer in a patient in need thereof, comprising administering to said patient a therapeutically efficient amount of Efavirenz, wherein said therapeutically efficient amount of Efavirenz generates an Efavirenz plasma concentration in said patient superior to 3000 ng/ml.

2. The method according to claim 1, wherein a suitable Efavirenz daily dose for the patient is determined based on Efavirenz plasma concentration monitoring.

3. The method according to claim 1, wherein a suitable Efavirenz daily dose for the patient is determined based on genotyping of the patient's CYP2B6 alleles.

4. The method of claim 1 wherein the patient does not have two loss or decrease of function CYP2B6 alleles.

5. The method according to claim 1, wherein the patient has two loss or decrease of function CYP2B6 alleles and the daily dose of Efavirenz administered to the patient is 600 mg.

6. The method of claim 1, wherein the patient is not infected by human immunodeficiency virus (HIV).

7. A method for treating prostate cancer in a patient in need thereof, comprising:
   a) administering a preliminary daily dose DP of Efavirenz to the patient,
   b) monitoring Efavirenz plasma concentration in the patient,
   c) administering an optimized daily dose DO of Efavirenz to the patient, wherein:
      i) if the patient's Efavirenz plasma concentration is inferior to 3000 ng/ml, then the optimized daily dose DO of Efavirenz is increased compared to the preliminary daily dose DP,
      ii) if the patient's Efavirenz plasma concentration is superior to 3000 ng/ml, then the optimized daily dose DO of Efavirenz is the same as or lower than the preliminary daily dose DP.

8. The method according to claim 7, which further comprises, before step a), a step of genotyping gene CYP2B6 of said patient.

9. The method of claim 7, wherein the patient is not infected by human immunodeficiency virus (HIV).

10. A method for treating prostate cancer in a patient in need thereof, comprising administering to said patient Efavirenz in one or two dosage units to generate an Efavirenz plasma concentration in said patient superior to 3000 ng/ml upon administration, and a pharmaceutically acceptable carrier.

11. The method of claim 10, wherein said dosage unit of Efavirenz is in the form of a tablet, capsule, powder, or granules.

* * * * *